US005824878A

United States Patent [19]

Ohba et al.

[11] Patent Number: 5,824,878

[45] Date of Patent: *Oct. 20, 1998

[54] MICROORGANISM AND INSECTICIDE

[75] Inventors: Michio Ohba, Fukuoka; Hidenori Iwahana; Ryoichi Sato, both of Tokyo; Nobukazu Suzuki, Ibaraki; Katsutoshi Ogiwara, Ibaraki; Kazunobu Sakanaka, Ibaraki; Hidetaka Hori, Kanagawa; Shouji Asano; Tadaaki Kawasugi, both of Ibaraki, all of Japan

[73] Assignee: Kubota Corporation, Japan

[ * ] Notice: The term of this patent shall not extend beyond the expiration date of Pat. No. 5,359,048.

[21] Appl. No.: 789,449

[22] Filed: Jan. 27, 1997

Related U.S. Application Data

[62] Division of Ser. No. 272,887, Jul. 8, 1994, Pat. No. 5,747, 450, which is a continuation of Ser. No. 915,203, Jul. 23, 1992, Pat. No. 5,359,048.

[51] Int. Cl.$^6$ ............................ A01H 5/00; A01N 63/00; C07H 21/04; C12N 1/21

[52] U.S. Cl. ......................... 800/205; 424/93.2; 424/405; 424/93.461; 435/252.1; 435/252.3; 435/348; 435/419; 536/23.71

[58] Field of Search .................................... 435/69.1, 348, 435/252.3, 252.31, 252.5; 536/23.1, 23.7, 23.71; 514/2; 424/93.2; 800/205

[56] References Cited

U.S. PATENT DOCUMENTS

| | | | |
|---|---|---|---|
| 4,966,765 | 10/1990 | Payne et al. | 424/93.461 |
| 5,064,648 | 11/1991 | Hickle et al. | 424/93.61 |
| 5,359,048 | 10/1994 | Ohba et al. | 536/23.71 |

FOREIGN PATENT DOCUMENTS

| | | |
|---|---|---|
| 2365188 | 8/1992 | Australia . |
| 7752691 | 8/1993 | Australia . |
| 0202739 | 11/1985 | European Pat. Off. . |
| 0337604 | 10/1989 | European Pat. Off. . |
| 0382990 | 8/1990 | European Pat. Off. . |
| 08901515 | 2/1989 | WIPO . |

OTHER PUBLICATIONS

Lambert et al., Appl. Enviro. Microbiol., vol. 58, No. 8, pp. 2536–2542, Aug. 1992.

Sato et al., Curr. Microbiol., vol. 28, pp. 15–19, 1994.

Couch, T.L. (1980) "Mosquito Pathogenicity of *Bacillus thuringiensis* var. *israelensis*" Developments in Industrial Microbiology 22:61–76.

Beegle, C.C. (1978) "Use of Entomogenous Bacteria in Agroecosystems" Developments in Industrial Microbiology 20:97–104.

Krieg, V.A. et al. (1983) "*Bacillus thuringiensis* var. *tenebrionis*: ein neuer, gegenuber Larven von Coleopteran wirksamer Pathotyp" Z. ang. Ent. 96:500–508.

Boswell et al. (1988) in *Computational Molecular Biology Sources and Methods for Sequence Analysis* (Leak, ed.) Oxford University Press, Oxford, pp. 170–171.

Ohba, M., H. Iwahana, S. Asano, N. Suzuki, R. Sato, H. Hori (1992) "A unique isolate of *Bacillus thuringiensis* serovar *japonensis* with a high larvicidal activity for scarabaeid beetles," *Letters in Applied Microbiology* 14:54–57.

Ohba, M., K. Aizawa (1986) "*Bacillus thuringiensis* subsp. *japonensis* (Flagellar Serotype 23): A new subspecies of *Bacillus thuringiensis* with a novel flagellar antigen," *J. Invert. Path.* 48:129–130.

Perlak, F.J., R. L. Fuchs, D.A. Dean, S.L. McPherson, D.A. Fischoff (1991) "Modification of the coding sequence enhances plant expression of insect control protein genes," *Proc. Natl. Acad. Sci.* 88:3324–3328.

Murray, E.E., T. Rocheleau, M. Eberle, C. Stock, V. Sekar, M. Adang (1991) "Analysis of unstable RNA transcripts of insecticidal crystal protein genes of *Bacillus thuringiensis* in transgenic plants and electroporated protoplasts," *Plant Molecular Biology* 16:1035–1050.

*Primary Examiner*—David Guzo

*Attorney, Agent, or Firm*—Saliwanchik, Lloyd & Saliwanchik

[57] ABSTRACT

*Bacillus thuringiensis* serovar *japonensis* strain Buibui (FERM BP-3465) belonging to *Bacillus thuringiensis* serovar *japonensis* and capable of producing insecticidal toxin proteins to kill coleopterous larvae, and an insecticide containing, as an effective ingredient, the toxin proteins produced.

15 Claims, 6 Drawing Sheets

MICROORGANISM AND INSECTICIDE

This subject application is a division of Ser. No. 08/272,887, filed Jul. 8, 1994 (now U.S. Pat. No. 5,947,450) which is a division of Ser. No. 07/915,203, filed Jul. 23, 1992 (now U.S. Pat. No. 5,359,048).

BACKGROUND OF THE INVENTION

1. Field of the Invention

This invention relates to a novel microorganism belonging to *Bacillus thuringiensis* serovar *japonensis,* to an insecticide derived from this novel microorganism, and to DNA coding for the insecticide.

2. Description of the Related Art

The reported activity spectrum of *B.t.* covers insect species within the order Lepidoptera, many of which are major pests in agriculture and forestry. The activity spectrum also includes the insect order Diptera, which includes mosquitos and black flies. See Couch, T. L. (1980) "Mosquito Pathogenicity of *Bacillus thuringiensis* var. *israelensis,*" *Developments in Industrial Microbiology* 22:61–76; Beegle, C. C., (1978) "Use of Entomogenous Bacteria in Agroecosystems," *Developments in Industrial Microbiology* 20:97–104. Krieg et al. (1983) *Z. ang. Ent.* 96:500–508, describe a *B.t.* isolate named *Bacillus thuringiensis* var. *tenebrionis,* which is reportedly active against two beetles in the order Coleoptera. These are the Colorado potato beetle, *Leptinotarsa decemlineata,* and *Agelastica alni.*

In European Patent Application 0 202 739 there is disclosed a novel *B.t.* isolate active against Coleoptera. It is known as *B. thuringiensis* var. *san diego* (*B.t.s.d.*). U.S. Pat. No. 4,966,765 discloses the coleopteran-active *Bacillus thuringiensis* isolate *B.t.* PS86B1. European Patent Application 0 337 604 also discloses a novel *B.t.* isolate active against Coleoptera.

Coleopteran-active *B.t.* strains can be used to control foliar-feeding beetles. The Colorado potato beetle (*Leptinotarsa decemlineata*), for example, is susceptible to the delta-endotoxin of *B.t.s.d.* and larvae are killed upon ingesting a sufficient dose of spore/crystal preparation on treated foliage. Strain cells among *Bacillus thuringiensis* serovar *japonensis* are known to produce insecticidal proteins that kill lepidopteran larvae. However, none of the strain cells among *japonensis* are known to produce toxin proteins other than the insecticidal proteins that kill lepidopterous larvae. Thus, no such strain cells have been available for use as an insecticide to kill insects other than lepidopterans. Furthermore, *Bacillus thuringiensis san diego* and *Bacillus thuringiensis tenebrionis* have no insecticidal effect on larvae of *Anomala cuprea* Hope, which are very destructive to firewood, taro, sweet potato, peanut, and the like.

The current inventors have found a new type of microorganism belonging to *Bacillus thuringiensis* serovar *japonensis* that produces insecticidal proteins to kill coleopterous larvae as distinct from lepidopterous larvae.

BRIEF SUMMARY OF THE INVENTION

The subject invention concerns a novel *Bacillus thuringiensis* (*B.t.*) isolate. The novel *B.t.* isolate, known as *Bacillus thuringiensis* serovar *japonensis* strain Buibui (hereinafter referred to as "*B.t.* Buibui"), has been found to be active against coleopteran pests including the Japanese beetle. A novel δ-endotoxin gene of the invention encodes an ≈130 kDa protein. The nucleotide sequence of this gene is shown in SEQ ID NO. 1. The predicted amino acid sequence of the toxin is shown in SEQ ID NO. 2.

The subject invention also includes variants of *B.t.* Buibui which have substantially the same pesticidal properties as *B.t.* Buibui. These variants would include mutants. Procedures for making mutants are well known in the microbiological art. Ultraviolet light and nitrosoguanidine are used extensively toward this end.

Further, the invention also includes the treatment of substantially intact *B.t.* cells, and recombinant cells containing a gene of the invention, to prolong the pesticidal activity when the substantially intact cells are applied to the environment of a target pest. Such treatment can be by chemical or physical means, or a combination of chemical or physical means, so long as the technique does not deleteriously affect the properties of the pesticide, nor diminish the cellular capability in protecting the pesticide. The treated cell acts as a protective coating for the pesticidal toxin. The toxin becomes available to act as such upon ingestion by a target insect.

BRIEF DESCRIPTION OF THE SEQUENCES

Figure 1:
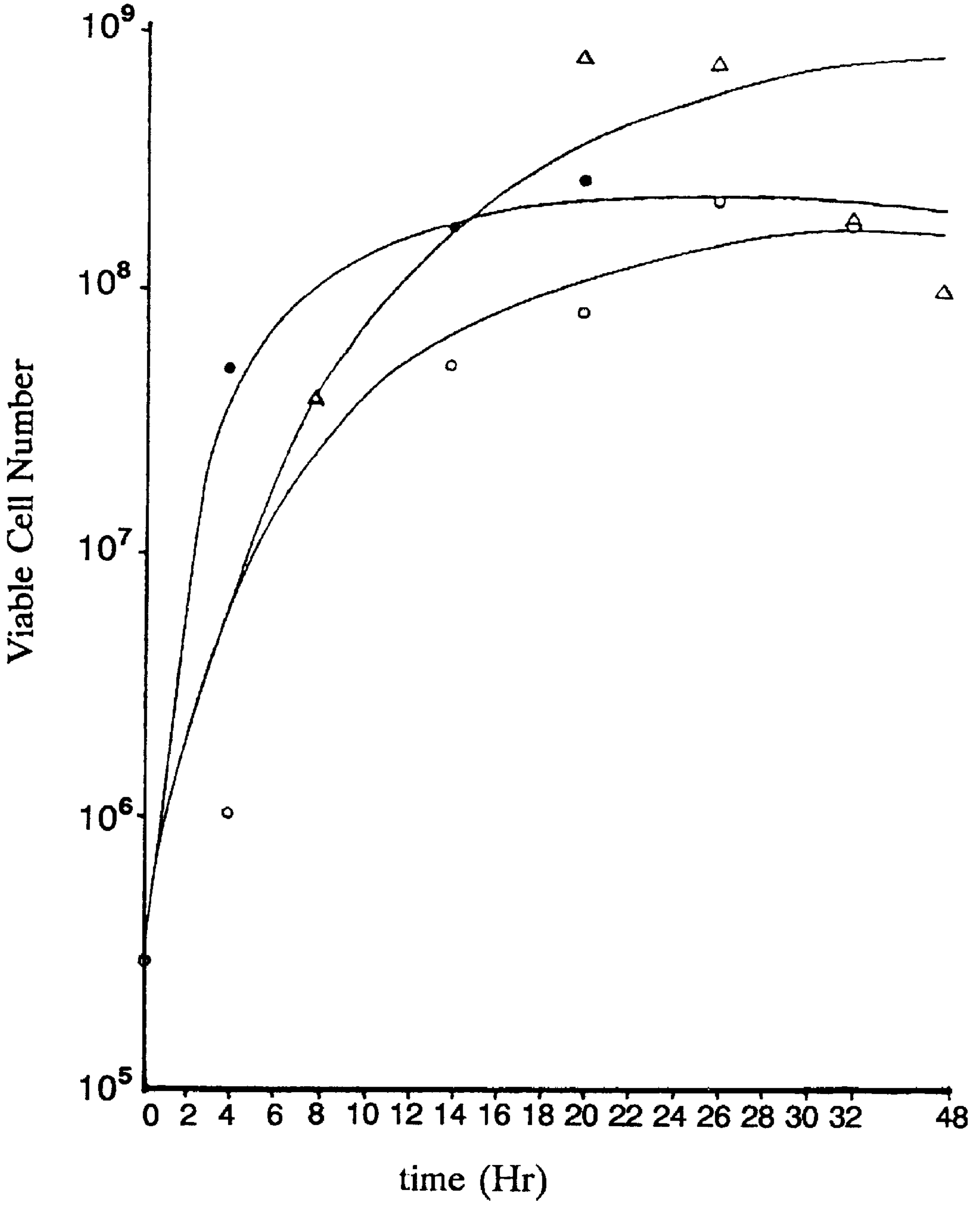
FIG. 1 is a graph showing growth curves of *B.t.* Buibui. The number of colonies produced by splaying the cells in the following agar culture media of the petri dish is measured. —●— LB medium; —○— NB medium; —Δ— NYS medium.

SEQ ID NO. 1 is the composite nucleotide and amino acid sequence of the novel gene of the invention.

SEQ ID NO. 2 is the predicted amino acid sequence of the toxin.

DETAILED DESCRIPTION OF THE INVENTION

The subject invention pertains to a novel strain of *Bacillus thuringiensis* which has the highly advantageous property of expressing at least one endotoxin which is toxic to coleopterans. The novel microorganism has been designated *Bacillus thuringiensis* serovar *japonensis* strain Buibui (hereinafter referred to as "*B.t.* Buibui"). The subject invention further pertains to insecticidal toxin obtainable from *B.t.* Buibui as well as DNA coding for said insecticide. Also disclosed and claimed are microorganisms, other than *Bacillus thuringiensis,* which have been transformed with *B.t.* Buibui DNA so that said transformed microbes express a coleopteran-active toxin. A further aspect of the subject invention is the use of a toxin of the subject invention, or a transformed host-expressing a toxin, to control coleopteran pests. Yet a further aspect of the subject invention pertains to plants transformed with a *B.t.* Buibui DNA coding for toxin active against coleopteran pests.

Novel microorganisms according to the present invention, have been deposited internationally, pursuant to the Treaty of Budapest, with the Fermentation Research Institute, Agency of Industrial Science and Technology, Ministry of International Trade and Industry, which is a recognized international depository organization.

| Culture | Deposit No. | Deposit Date |
|---|---|---|
| *Bacillus thuringiensis* serovar *japonensis* strain *Buibui* | FERM BP-3465 | June 26, 1992 |
| *Escherichia Coli* KBR9207 | FERM BP-3929 | ??? |

The subject cultures have been deposited under conditions that assure that access to the cultures will be available during the pendency of this patent application to one determined by the Commissioner of Patents and Trademarks to be entitled thereto under 37 CFR 1.14 and 35 U.S.C. 122. The deposits are available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of a deposit, and in any case, for a period of at least thirty (30) years after the date of deposit or for the enforceable life of any patent which may issue disclosing the cultures. The depositor acknowledges the duty to replace the deposits should the depository be unable to furnish a sample when requested, due to the condition of the deposits. All restrictions on the availability to the public of the subject culture deposits will be irrevocably removed upon the granting of a patent disclosing them.

The invention also includes variants of the subject isolates which variants have genes encoding all or part of a toxin of the invention. Such microbial variants may be isolated or they can be made by techniques well known to persons skilled in the art. For example, UV irradiation can be used to prepare variants of host organisms. Likewise, such variants may include asporogenous host cells which also can be prepared by procedures well known in the art. For example, an asporogenous mutant can be obtained through ethylmethane sulfonate (EMS) mutagenesis of a novel isolate. A small percentage of the asporogenous mutants will remain intact and not lyse for extended fermentation periods; these strains are designated lysis minus (–). Lysis minus strains can be identified by screening asporogenous mutants in shake flask media and selecting those mutants that are still intact and contain toxin crystals at the end of the fermentation. Lysis minus strains are suitable for a cell fixation process that will yield a protected, encapsulated toxin protein.

To prepare a phage resistant variant of said asporogenous mutant, an aliquot of the phage lysate is spread onto nutrient agar and allowed to dry. An aliquot of the phage sensitive bacterial strain is then plated directly over the dried lysate and allowed to dry. The plates are incubated at 30° C. The plates are incubated for 2 days and, at that time, numerous colonies could be seen growing on the agar. Some of these colonies are picked and subcultured onto nutrient agar plates. These apparent resistant cultures are tested for resistance by cross streaking with the phage lysate. A line of the phage lysate is streaked on the plate and allowed to dry. The presumptive resistant cultures are then streaked across the phage line. Resistant bacterial cultures show no lysis anywhere in the streak across the phage line after overnight incubation at 30° C. The resistance to phage is then reconfirmed by plating a lawn of the resistant culture onto a nutrient agar plate. The sensitive strain is also plated in the same manner to serve as the positive control. After drying, a drop of the phage lysate is plated in the center of the plate and allowed to dry. Resistant cultures showed no lysis in the area where the phage lysate has been placed after incubation at 30° C. for 24 hours.

The variants can also be made using ultraviolet light and nitrosoguanidine by procedures well known in the art.

The novel microorganism, *B.t.* Buibui, specifically exemplified according to the present invention has the following characteristics:

1. Growth in Different Culture Media

Figure 2:
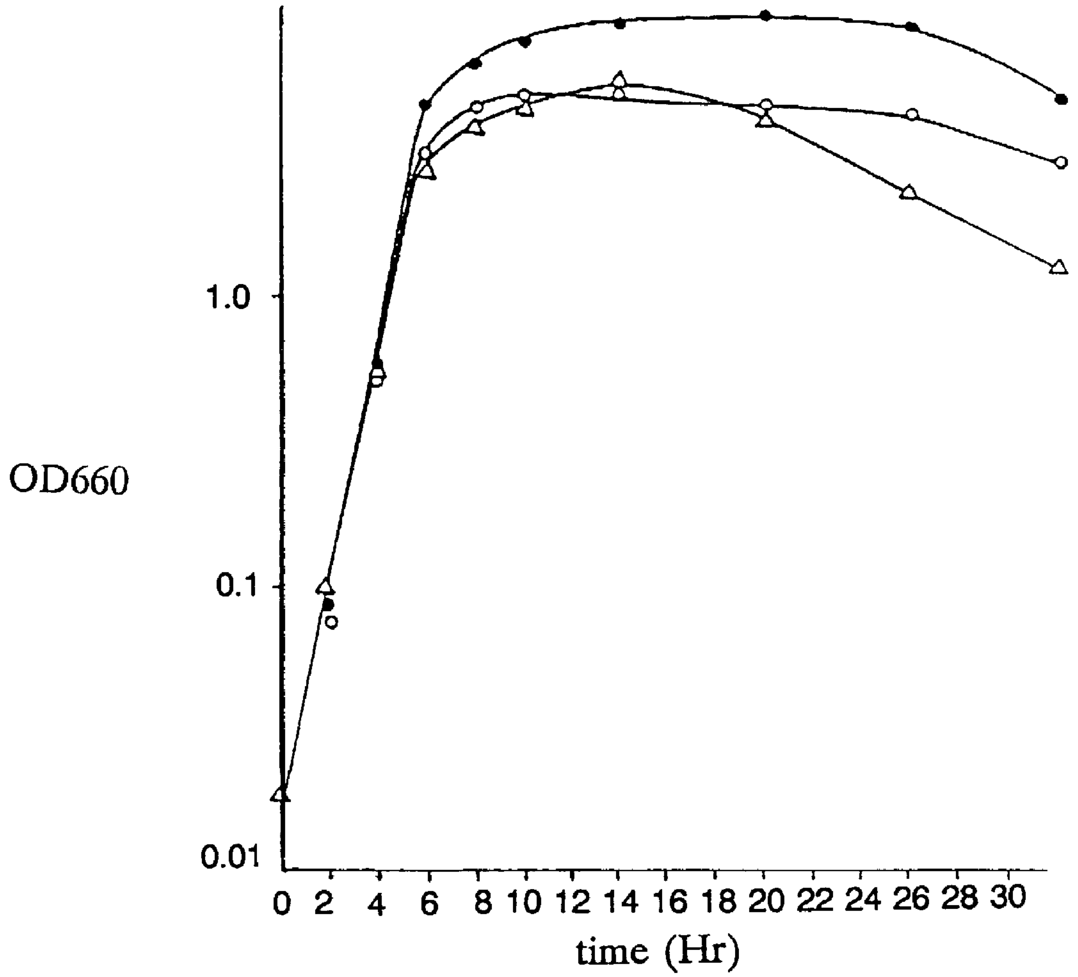
FIG. 2 is a graph showing growth curves of *B.t.* Buibui. The increase of the number of cells is shown by the absorptive increase of media at 660 nm. —●— LB medium; —○— NB medium; —Δ— NYS medium.

This microorganism may be grown and the toxin proteins may be produced in all types of media that can be used for culturing ordinary bacteria. As shown in FIGS. 1 and 2, the microorganism showed ordinary growth patterns in typical culture media such as NYS, L-broth, and bouillon media. That is, the number of cells began to increase logarithmically after lapse of several hours, and the increase stopped upon lapse of 24 hours. Toxins appeared slightly after the increase in the number of cells. The quantity of toxins, when measured in the main band 130 kDa, was 200 to 300 $\mu$g/ml medium.

2. Morphological Characteristics

Figure 3:
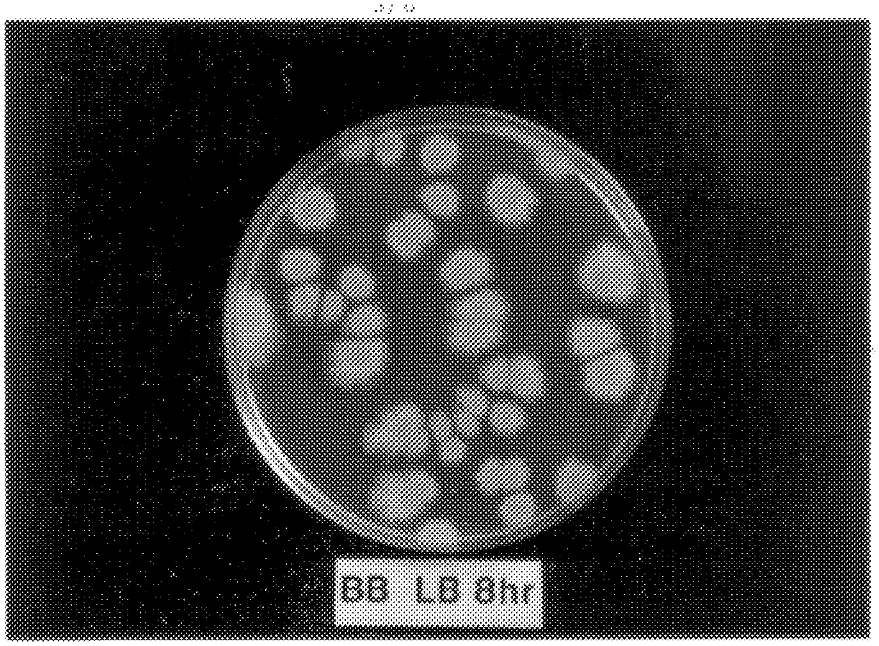
FIG. 3 is a photograph showing colonies of *B.t.* Buibui in LB culture medium. The colonies of Buibui strain were cultured in the LB agar culture media for 72 hours after being cultured in the LB culture media for 8 hours.
Figure 4:
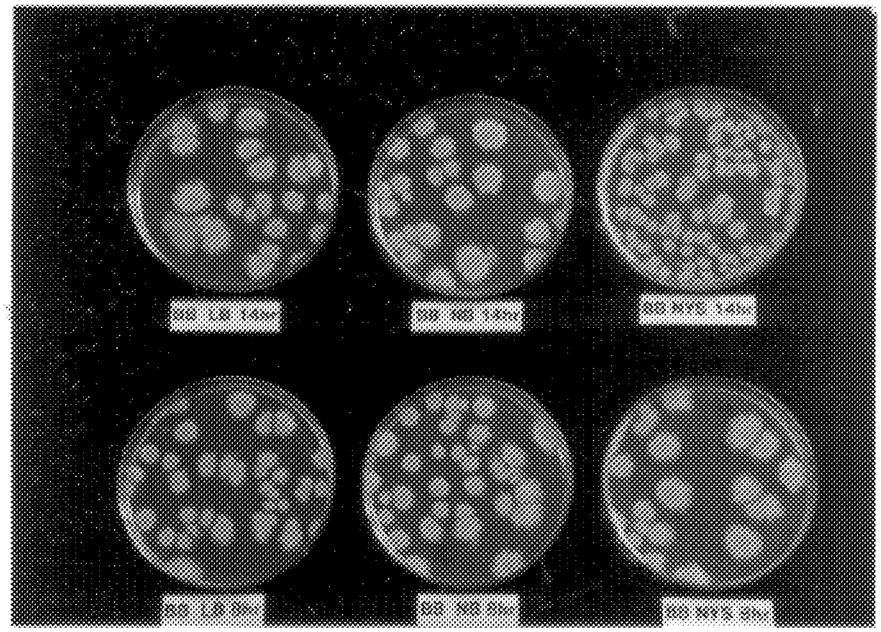
FIG. 4 is a photograph showing colonies of *B.t.* Buibui in various culture media. The colonies of Buibui strain were cultured in the respective agar culture media for 72 hours after being cultured in the LB, NB, and NYS culture media for 8 hours and 14 hours.

As shown in FIGS. 3 and 4, the colonies produced have surface gloss on an agar medium, and spread thinly over the agar surfaces without swelling. Peripheral roughs show characteristics of ordinary Bacillus cells. The color of the colonies is light beige.

When observed through a scanning electron microscope, both *Bacillus thuringiensis* serovar *japonensis* and *Bacillus thuringiensis* serovar *japonensis* strain Buibui show spherical crystal proteins. These are distinct from the bipyramid crystals commonly observed with other *B.t.* cells lethal to lepidopterous larvae.

3. Biochemical Appearance

The following tests have been conducted to evaluate the biochemical characteristics of *B.t.* Buibui as compared with conventional *japonensis* strains:

Test 1

Serotyping using antibodies produced against flagellar antigens: This is a method for identifying an unknown organism by employing an antibody active to the proteins of flagella of Bacillus organisms, and utilizing an antigen-antibody reaction in which the flagellar proteins of the unknown organism act as the antigens. *japonensis* strain is a subspecies classified and recognized as H23 type (*J. Invertebr. Pathol.* 32:303–309, 1978; *J. Invertebr. Pathol.* 48:129–130, 1986). *B.t.* Buibui is reactive with H-antigen of *japonensis* strain. This property is serologically equivalent to that of *japonensis* strain. Thus, taxonomically, *B.t.* Buibui belongs to the same subspecies as *japonensis* strain. Details of this test are as follows:

(1) Preparation of flagellar H-serum

Forty known types of H-antigen standard strains of *Bacillus thuringiensis* were used. Microorganisms having excellent mobility were selected by using a Craigie tube (0.5% semifluid agar medium), and formalin-killed organisms were prepared. Rabbits were immunized with these organisms. H-serum was prepared by absorbing, from respective antisera, antibodies reactive to *Bacillus thuringiensis* cell antigens. The cell antigens were prepared by heating them to 100° C. and separating the flagella.

(2) Identification of H-antigen

Serum types of H-antigen were identified through agglutination reactions on slide glass (Ohba and Aizawa [1978] *J. Invertebr. Pathol.* 32:303–309). Agglutination values of H-serum were measured through in vitro agglutination reactions (Ohba and Aizawa, supra).

(3) Results

*japonensis* strain was particularly agglutinated only by the serum for standard strain cells of serovar *japonensis* (H-antigen 23) among standard sera including 40 known types of flagellar antigens only. The agglutination value of *japonensis* H-serum for corresponding homo-antigens was 12,800-fold, and the agglutination value thereof for Buibui strain was 6,400-fold. The agglutination value of *B.t.* Buibui H-serum for homo was 12,800-fold and the agglutination value thereof for *japonensis* standard strain was 6,400-fold. Thus, the two strain cells are determined to be the same species.

Test 2

Insecticidal spectral of crystal proteins produced by *japonensis* strain and *B.t.* Buibui: As shown in Table 1, the insecticidal proteins produced by *B.t.* Buibui showed an insecticidal effect in a concentration of 0.125 to 12.5 μg/ml on *Anomala cuprea* Hope, a coleopteran. However, the insecticidal proteins produced by the *japonensis* strain did not show an insecticidal effect even in a concentration of 100 μg/ml. As shown in Table 2, the insecticidal proteins produced by *japonensis* strain showed a high degree of activity with respect to larvae of lepidopterans such as *Plutella xylostella, Adoxophyes sp.,* and *Bombyx mori.* However, the insecticidal proteins produced by *B.t.* Buibui showed little or a very low degree of activity. These results demonstrate that the two strains cannot be said to be the same strains.

Furthermore, the observance of coleopteran activity, but no lepidopteran activity is quite surprising and unexpected.

TABLE 1

Insecticidal effects of *japonensis* strain and *B.t. Buibui* on *Anomala cuprea* Hope

| Toxin dosage (μg 130 kDa protein/ml) | Death rates* (%) 7th day | 14th day | 22nd day |
|---|---|---|---|
| *B.t. Buibui* cells | | | |
| 12.5 | 65 | 95 | 95 |
| 1.25 | 45 | 95 | 100 |
| 0.125 | 0 | 30 | 80 |
| *Japonensis* strain cells 100 | 0 | 0 | 0 |

*Number of samples = 20 larvae in the first instar.

TABLE 2

Insecticidal activities of *japonensis* strain and *Buibui* strain with respect to some lepidopterans.

| Samples | Toxin dosage (μg 130 kDa protein/ml) | Death rates* (%) *Buibui* | *japonensis* |
|---|---|---|---|
| *Plutella xylostella* | 50 | 0 | 100 |
| *Spodoptera litura* | 500 | 0 | — |
| | 50 | 0 | 4 |
| Adoxophyes sp. | 50 | 6 | 47 |
| *Spodoptera exigua* | 50 | 10 | 3 |
| *Bombyx mon* | 50 | 0 | 70 |

*Number of samples = 50 larvae in the first to third instar.

Test 3

Figure 5:
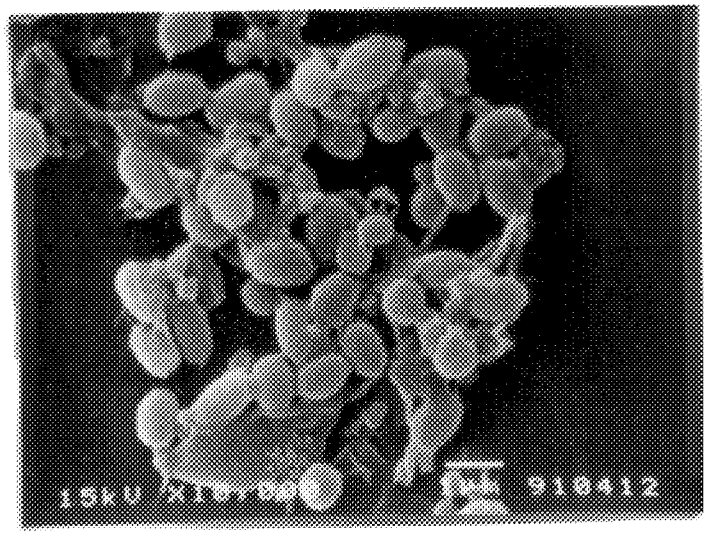
FIG. 5 is a photograph of japonensis strain taken with a scanning electron microscope. The dark arrows show crystals of toxin proteins. The elliptic members having wrinkled surfaces are spores.
Figure 6:
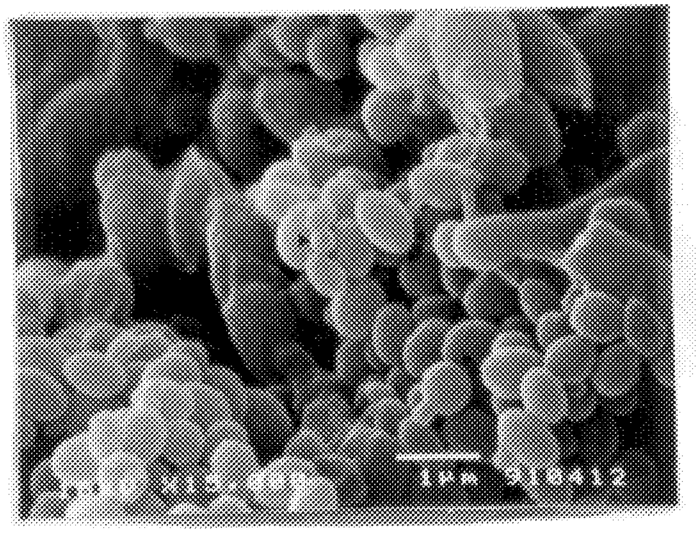
FIG. 6 is a photograph of *B.t.* Buibui taken with the scanning electron microscope. The dark arrows show crystals of toxin proteins. The elliptic members having wrinkled surfaces are spores.
Figure 7:
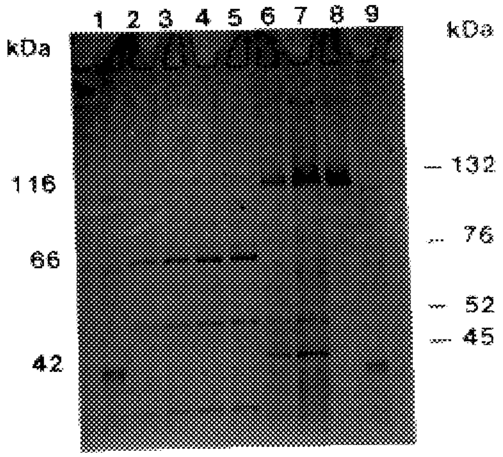
FIG. 7 is a photograph showing sodium dodecyl sulfate polyacrylamide gel electrophoresis. Lane 1 is a molar weight marker. Lane 2 shows toxin proteins produced by japonensis strain (5 μl). Lane 3 shows toxin proteins produced by *japonensis* strain (10 μl). Lane 4 shows toxin proteins produced by *japonensis* strain (15 μl). Lane 5 shows toxin proteins produced by *japonensis* strain (20 μl). Lane 6 shows toxin proteins produced by Buibui strain (5 μl). Lane 7 shows toxin proteins produced by Buibui strain (10 μl). Lane 8 shows toxin proteins produced by Buibui strain (5 μl). Lane 9 is a molar weight marker.

Electrophoresis of insecticidal proteins accumulating in the cells of *japonensis* strain and *B.t.* Buibui: *B.t.* Buibui produces, in the cells, spherical crystalline proteins as does *japonensis* strain (FIGS. 5 and 6). The crystalline proteins were isolated from the culture medium by a standard method (Goodman, N. S., R. J. Gottfried, M. J. Rogoff [1987] *J. Bacteriol.* 34:485). After purification, the proteins were dissolved in a 0.4N alkali solution, and analyzed through sodium dodecyl sulfate polyacrylamide gel electrophoresis (SDS-PAGE). As shown in FIG. 7, *japonensis* strain has a main band at about 76 kDa, and a different band at 52 kDa. *B.t.* Buibui has a main band at about 130 kDa, and different bands at 52 kDa and 45 kDa. These electrophoresis patterns clearly show that the two types of crystalline proteins have different ingredients.

Test 4

Difference in adoptivity in culture media between *japonensis* strain and *B.t.* Buibui: As shown in Table 3, *japonensis* strain adopts glucose, salicin, and maltose, does not adopt mannose, and adopts cellobiose to a certain degree. *B.t.* Buibui can adopt all of these substances.

These features show that, taxonomically, *B.t.* Buibui is classified by serotype as *japonensis* strain, but clearly is a cell different from *japonensis* strain.

TABLE 3

| | *japonensis* | *Buibui* |
|---|---|---|
| Sugars | | |
| glucose | ++ | ++ |
| D-(+)-xylose | − | − |

TABLE 3-continued

| | japonensis | Buibui |
|---|---|---|
| D-(+)-arabinose | − | − |
| mannitol | − | − |
| galactose | − | − |
| mannose | − | ++ |
| salicin | ++ | ++ |
| sucrose | +− | +− |
| D-(+)-cellobiose | +− | ++ |
| maltose | ++ | ++ |
| lactose | − | − |
| acetoin | + | + |
| urease | ++ | ++ |

+++ = adopt very well; + = adopt well, +− = adopt; − = do not adopt

*B.t.* Buibui can be cultured using standard art media and fermentation techniques. Specific examples of fermentation media and techniques are provided in the examples which follow. Upon completion of the fermentation cycle, the bacteria can be harvested by first separating the *B.t.* spores and crystals from the fermentation broth by means well known in the art. The recovered *B.t.* spores and crystals can be formulated into a wettable powder, liquid concentrate, granules, or other formulations by the addition of surfactants, dispersants, inert carriers and other components to facilitate handling and application for particular target pests. These formulation and application procedures are all well known in the art.

DNA containing the toxin gene from *B.t.* Buibui can be purified from *E. coli* KBR9207 by standard procedures well known in the art. The toxin gene can be excised from the plasmid DNA by restriction enzyme digestion. This subject invention pertains not only to the specific DNA sequence shown in SEQ ID NO. 1, but also to variations of this sequence which code for an amino acid sequence having activity against coleopteran characteristics of the toxin produced by *B.t.* Buibui. These DNA sequences would be expected to have a high degree of homology and, for example, would be expected to hybridize with each other and/or common probes or primers under high stringency conditions. Similarly, the subject invention pertains not only to the protein having the amino acid sequence shown in SEQ ID NO. 2, but also to equivalent toxins having the same or similar biological activity of the toxin shown in SEQ ID NO. 2. These equivalent toxins may have amino acid homology with the toxin disclosed and claimed herein. This amino acid homology will typically be greater than 50%, preferably be greater than 75%, and most preferably be greater than 90%. The amino acid homology will be highest in certain critical regions of the toxin which account for biological activity or are involved in the determination of three-dimensional configuration which ultimately is responsible for the biological activity. In this regard, certain amino acid substitutions are acceptable and can be expected if these substitutions are in regions which are not critical to activity or are conservative amino acid substitutions which do not affect the three-dimensional configuration of the molecule. For example, amino acids may be placed in the following classes: nonpolar, uncharged polar, basic, and acidic. Conservative substitutions whereby an amino acid of one class is replaced with another amino acid of the same type fall within the scope of the subject invention so long as the substitution does not materially alter the biological activity of the compound. Table 4 provides a listing of examples of amino acids belonging to each class.

TABLE 4

| Class of Amino Acid | Examples of Amino Acids |
|---|---|
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

In some instances, non-conservative substitutions can also be made. The critical factor is that these substitutions must not significantly detract from the biological activity of the toxin.

The genes and toxins according to the subject invention include not only the full length sequences disclosed herein but also fragments of these sequences, or fusion proteins, which retain the characteristic coleopteran activity of the toxins specifically exemplified herein.

It should be apparent to a person skilled in this art that genes coding for coleopteran-active toxins can be identified and obtained through several means. The specific genes may be obtained from a culture depository as disclosed herein. Alternatively, these genes, or portions thereof, may be constructed synthetically, for example, by use of a gene machine. Variations of these genes may be readily constructed using standard techniques for making point mutations. Also, fragments of these genes can be made using commercially available exonucleases or endonucleases according to standard procedures. For example, enzymes such as Bal31 or site-directed mutagenesis can be used to systematically cut off nucleotides from the ends of these genes. Also, genes which code for active fragments may be obtained using a variety of other restriction enzymes. Proteases may be used to directly obtain active fragments of these toxins.

DNA of the subject invention, which codes for coleopteran-active toxin, can be introduced into a wide variety of microbial and plant hosts. Expression of the DNA results, directly or indirectly, in the production and maintenance of the pesticide. With suitable hosts, e.g., Pseudomonas, the microbes can be applied to the situs of coleopteran insects where they will proliferate and be ingested by the insects. The result is a control of the unwanted insects. Alternatively, a microbe hosting the toxin-coding DNA can be treated under conditions that prolong the activity of the toxin produced in the cell. The treated cell then can be applied to the environment of target pest(s). The resulting product retains the toxicity of the *B.t.* toxin.

Where the *B.t.* toxin-coding DNA is introduced via a suitable vector into a microbial host, and said host is applied to the environment in a living state, it is essential that certain host microbes be used. Microorganism hosts are selected which are known to occupy the "phytosphere" (phylloplane, phyllosphere, rhizosphere, and/or rhizoplane) of one or more crops of interest. These microorganisms are selected so as to be capable of successfully competing in the particular environment (crop and other insect habitats) with the wild-type microorganisms, provide for stable maintenance and expression of the gene expressing the polypeptide pesticide, and, desirably, provide for improved protection of the pesticide from environmental degradation and inactivation.

A large number of microorganisms are known to inhabit the phylloplane (the surface of the plant leaves) and/or the rhizosphere (the soil surrounding plant roots) of a wide variety of important crops. These microorganisms include bacteria, algae, and fungi. Of particular interest are microorganisms, such as bacteria, e.g., genera Pseudomonas, Erwinia, Serratia, Klebsiella, Xanthomonas, Streptomyces, Rhizobium, Rhodopseudomonas, Methylophilius, Agrobacterium, Acetobacter, Lactobacillus, Arthrobacter, Azotobacter, Leuconostoc, and Alcaligenes; fungi, particularly yeast, e.g., genera Saccharomyces, Cryptococcus, Kluyveromyces, Sporobolomyces, Rhodotorula, and Aureobasidium. Of particular interest are such phytosphere bacterial species as *Pseudomonas syringae, Pseudomonas fluorescens, Serratia marcescens, Acetobacter xylinum, Agrobacterium tumefaciens, Rhodopseudomonas spheroides, Xanthomonas campestris, Rhizobium melioti, Alcaligenes entrophus,* and *Azotobacter vinlandii;* and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae,* and *Aureobasidium pollulans.* Of particular interest are the pigmented microorganisms.

A wide variety of ways are available for introducing the *B.t.* DNA expressing the toxin into the microorganism host under conditions which allow for stable maintenance and expression of the gene. These methods are well known and easily practiced by those skilled in this art. The transformants can be isolated in accordance with conventional ways, usually employing a selection technique, which allows for selection of the desired organism as against unmodified organisms or transferring organisms, when present. The transformants then can be tested for pesticidal activity.

The *B.t.* cells can be treated prior to formulation to prolong the pesticidal activity when the cells are applied to the environment of a target pest. Such treatment can be by chemical or physical means, or by a combination of chemical and/or physical means, so long as the technique does not deleteriously affect the properties of the pesticide, nor diminish the cellular capability in protecting the pesticide. Examples of chemical reagents are halogenating agents, particularly halogens of atomic no. 17–80. More particularly, iodine can be used under mild conditions and for sufficient time to achieve the desired results. Other suitable techniques include treatment with aldehydes, such as formaldehyde and glutaraldehyde; anti-infectives, such as zephiran chloride; alcohols, such as isopropyl and ethanol; various histologic fixatives, such as Bouin's fixative and Helly's fixative (See: Humason, Gretchen. L., *Animal Tissue Techniques,* W. H. Freeman and Company, 1967); or a combination of physical (heat) and chemical agents that prolong the activity of the toxin produced in the cell when the cell is applied to the environment of the target pest(s). Examples of physical means are short wavelength radiation such as gamma-radiation and X-radiation, freezing, UV irradiation, lyophilization, and the like. The cell will usually be intact and be substantially in the proliferative form when treated, rather than in a spore form, although in some instances spores may be employed.

The treated cells generally will have enhanced structural stability which will enhance resistance to environmental conditions. Where the pesticide is in a proform, the method of inactivation should be selected so as not to inhibit processing of the proform to the mature form of the pesticide by the target pest pathogen. For example, formaldehyde will crosslink proteins and could inhibit processing of the proform of a polypeptide pesticide. The method of inactivation or killing retains at least a substantial portion of the bioavailability or bioactivity of the toxin.

The cellular host containing the *B.t.* insecticidal gene may be grown in any convenient nutrient medium, where the DNA construct provides a selective advantage, providing for a selective medium so that substantially all or all of the cells retain the *B.t.* gene. These cells may then be harvested in accordance with conventional ways. Alternatively, the cells can be treated prior to harvesting.

The *B.t.* or transformed cells may be formulated in a variety of ways. They may be employed as wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, gels, suspensions, emulsifiable concentrates, or the like. The ingredients may include Theological agents, surfactants, emulsifiers, dispersants, or polymers.

Another approach that can be taken is to incorporate the spores and crystals of *B.t.* Buibui into bait granules containing an attractant and applying these granules to the soil for control of soil-inhabiting Coleoptera. Formulated *B.t.* Buibui can also be applied as a seed-coating or root treatment or total plant treatment.

The pesticidal concentration will vary widely depending upon the nature of the particular formulation, particularly whether it is a concentrate or to be used directly. The pesticide will be present in at least 1% by weight and may be 100% by weight. The dry formulations will have from about 1–95% by weight of the pesticide while the liquid formulations will generally be from about 1–60% by weight of the solids in the liquid phase. The formulations will generally have from about $10^2$ to about $10^4$ cells/mg. These formulations will be administered at about 50 mg (liquid or dry) to 1 kg or more per hectare.

The formulations can be applied to the environment of the coleopteran pest(s), e.g., plants, soil or water, by spraying, dusting, sprinkling, or the like.

Following are examples which illustrate procedures, including the best mode, for practicing the invention. These examples should not be construed as limiting. All percentages are by weight and all solvent mixture proportions are by volume unless otherwise noted.

EXAMPLE 1

Culturing *B.t.* Buibui

A subculture of *B.t.* Buibui can be used to inoculate the following medium, a peptone, glucose, salts medium.

| | |
|---|---|
| Bacto Peptone | 7.5 g/l |
| Glucose | 1.0 g/l |
| $KH_2PO_4$ | 3.4 g/l |
| $K_2HPO_4$ | 4.35 g/l |
| Salt Solution | 5.0 ml/1 |
| $CaCl_2$ Solution | 5.0 ml/1 |
| Salts Solution (100 ml) | |
| $MgSO_4.7H_2O$ | 2.46 g |
| $MnSO_4.H_2O$ | 0.04 g |
| $ZnSO_4.7H_2O$ | 0.28 g |
| $FeSO_4.7H_2O$ | 0.40 g |
| $CaCl_2$ Solution (100 ml) | |
| $CaCl_2.2H_2O$ | 3.66 g |
| pH | 7.2 |

The salts solution and $CaCl_2$ solution are filter-sterilized and added to the autoclaved and cooked broth at the time of inoculation. Flasks are incubated at 30° C. on a rotary shaker at 200 rpm for 64 hr.

The above procedure can be readily scaled up to large fermentors by procedures well known in the art.

The *B.t.* spores and crystals, obtained in the above fermentation, can be isolated by procedures well known in the art. A frequently-used procedure is to subject the harvested fermentation broth to separation techniques, e.g., centrifugation.

EXAMPLE 2

Further Methods for Culturing *B.t.* Buibui

*B.t.* Buibui easily grows in culture media commonly used for culturing bacteria, such as L-broth, nutrient broth, and the like, and produces spores and crystalline proteins. Inventors have reviewed highly productive media for culturing *B.t.* Buibui to produce insecticidal ingredients including the crystalline proteins.

First, $3.3\times10^5$ spores were inoculated into an agar medium on a 9 cm petri dish. The crystalline proteins produced in 10 days were observed through a microscope. A medium having $MnSO_4$ (10-#M) added to L-broth was the most productive, the order of productivity being as follows:

L-broth+$MnSO_4$>spizizen+amino acid>L-broth>PGSM>spizizen+casamino acid+vitamin>spizizen+casamino acid>NYS>NYS+casamino acid.

The respective media have the following compositions:

L-broth: 10 g of tryptose, 5 g of yeast extract, and 5 g of table salt, all per 1 liter, and pH=7.18 to 7.2.

Spizizen: 14 g of potassium 1-hydrogen phosphate ($K_2H$), 6 g of potassium 2-hydrogen phosphate ($KH_2PO_4$), 2 g of ammonium sulfate, 0.2 g of magnesium sulfate, 1 g of sodium citrate, and 5 g of glucose, all per 1 liter, and pH=7.0.

NYS: 1.25 g of nutrient broth, 1.25 g of trypton, 0.5 g of yeast extract, 10.3 g of calcium chloride, 20.35 g of magnesium chloride, 1.0 g of manganese chloride, 0.02 g of iron sulfate, and 0.02 g of zinc sulfate, all per 1 liter, and pH=7.2.

NYS+casamino acid: 2.0 g of casamino acid added to the above NYS medium, and pH=7.2.

Next, in preparing an insecticide using the insecticidal crystalline proteins produced by the subject cells and effective on coleopterous larvae, the microorganisms according to the invention are cultured in the various media noted above, or in solid media such as fish meal, soy bean powder and the like, or in wastes from starch or sugar processing such as corn syrup and corn steep. The cells cultured by the various methods as above are condensed into creamy form. This is appropriately diluted with water or the like to be sprayed as an insecticide. An antiseptic, extender, and the like, may be mixed into the creamy substance by a usual method. The creamy substance may subsequently be reduced to powder form by means of a spray dryer.

The above method uses the cells themselves which produce the toxin proteins. However, only the crystalline proteins may be used after culturing the cells until autolysis. The product thus obtained is used as a viable microbe cell preparation since the cells produce spores. The toxin proteins produced by these cells do not show toxicity to *Bombyx mori*. Thus, use of the viable microbe cell preparation having spores is not destructive at all to silk culture. Further, the spores may be killed with a suitable compound for use as a killed microbe cell preparation.

A method of spraying the above preparation will be described next. Coleopterous larva to be killed usually live in soil. Thus, the insecticide having the subject cells as an effective ingredient may be sprayed into soil, or may be scattered together with leaf mold which is immediately followed by a mixing operation with a cultivator or the like. A suspension of the above insecticide may be injected directly into soil by using an automatic or manual injector or the like. For this purpose, a fully automatic injector may be installed on a cultivator.

EXAMPLE 3

Insecticidal Activity of *B.t.* Buibui with Respect to *Anomala cuprea* Hope, a Coleopteran As noted hereinabove, Buibui strain shows a very high degree of insecticidal activity not reported heretofore, with respect to *Anomala cuprea* Hope. The insecticidal activity of *B.t.* Buibui was examined using larvae of *Anomala cuprea* Hope in the first to third instars.

The activity was evaluated as follows: 2 ml of water containing insecticidal ingredients was added to 2 g of dry leaf mold. The mixture was placed in a plastic cup. The larvae were then placed one after another and kept therein for a predetermined time.

The insecticidal ingredients included a culture solution of Buibui strain (i.e., a solution containing Buibui strain cells) and crystalline toxin proteins isolated from the culture solution and purified. The insecticidal activity of each ingredient was examined. It is to be noted that the death rate is the number of dead larvae divided by the total number of larvae.

Figure 8:
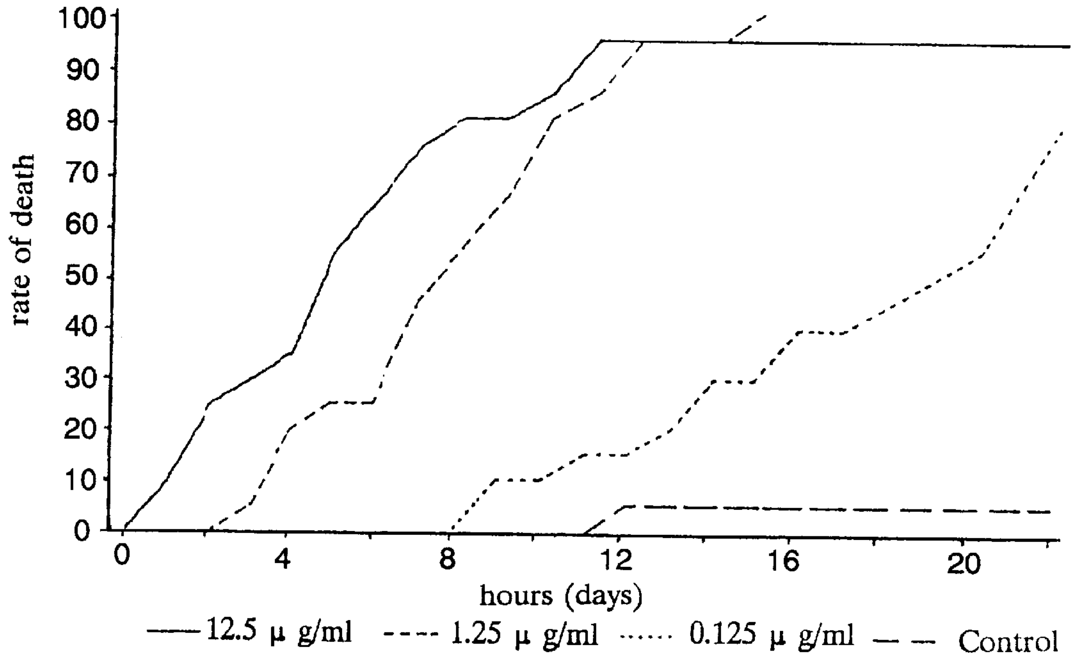
FIG. 8 is a graph showing time-dependent death curves of larvae of *Anomala cuprea* Hope. ——— 12.5 μg/ml; ----- 1.25 μg/ml; ..... 0.125 μg/ml; —— —— control.

FIG. 8 shows how the death rate varies with lapse of time depending on quantity of the insecticidal ingredient (toxin) comprising the culture solution. It will bee seen that 100% death rate is obtained with a low toxin dosage of 0.125 μg/ml and with a high dosage of 12.5 μg/ml. It has been found, however, that twice the time is taken before all the larvae were killed in the case of a low concentration.

The term "control" in FIG. 8 signifies variations occurring when only water containing no toxin is applied.

As shown in Table 5, the insecticidal ingredient comprising the crystalline proteins isolated and purified, showed insecticidal activity on its own. No insecticidal activity was detected with crystals 0.1 μg/ml. However, 100% death rate was obtained, though slowly, when the culture solution containing 130 kDa proteins in 1 μg/ml was applied to *Anomala cuprea* Hope as noted hereinabove (FIG. 8). This is considered due to the fact that spores present in the cells cooperate with the crystalline proteins in *Anomala cuprea* Hope to show the high degree of activity, and not that activity is lost due to denaturation of the proteins in the course of purification of the crystalline proteins. Thus, the insecticide may contain the cells.

TABLE 5

Insecticidal activities of culture solution and crystalline proteins of *Buibui* strain with respect to *Anomala cuprea* Hope

| Toxin dosage (μg 130 kDa protein/ml) | Death rates* (%) 7th day | 14th day | 21st day |
|---|---|---|---|
| Culture solution | | | |
| 10 | 60 | 100 | |
| 1 | 40 | 95 | 100 |

TABLE 5-continued

Insecticidal activities of culture solution and crystalline proteins of *Buibui* strain with respect to *Anomala cuprea* Hope

| Toxin dosage | Death rates* (%) | | |
|---|---|---|---|
| (μg 130 kDa protein/ml) | 7th day | 14th day | 21st day |
| Crystalline proteins | | | |
| 10 | 50 | 100 | |
| 1 | 0 | 10 | 20 |
| 0.1 | 0 | 0 | 0 |

*Number of samples = 20 larvae in the first instar. The cells were cultured in NYS.

EXAMPLE 4

Insecticidal Effects of *B.t.* Buibui on Larvae of Other Coleopterans

As shown in Table 6, Buibui strain showed a higher degree of insecticidal activity with respect also to *Anomala rufocuprea* Motschulsky, *Anomala schoenfeldti* Ohaus, apart from *Anomala cuprea* Hope. Thus, Buibui strain is expected to show insecticidal effect on larvae of several other *Minela splendens*. Thus, the insecticide is not limited in application to these three types of coleopterans.

TABLE 6

Insecticidal activities of crystalline proteins produced by *Buibui* strain with respect to *Anomala rufocuprea* Motschulsky and *Anomala schoenfeldti* Ohaus

| Insects | Toxin dosage (μg 130 kDa protein/ml) | Death rates 4 | 7 | 10 | 14 | 18 | 21st days |
|---|---|---|---|---|---|---|---|
| *Anomala schoenfeldti* Ohaus | 50 | 0 | 10 | 20 | 30 | 60 | 90 |
| *Anomala rufocuprea* Motschulsky | 50 | 0 | 10 | 20 | 30 | 60 | 100 |
| Larvae in 3rd instar of *Anomala rufocuprea* Motschulsky | 50 | 0 | 10 | 30 | 30 | 70 | 90 |
| Control | 0 | 0 | 0 | 0 | 0 | 0 | 10 |

The insects other than the larvae in the third instar of *Anomala rufocuprea* Motschulsky were all larvae in the first instar. The crystals were purified from cells cultured in NYS. The number of samples was 10.

The term "control" above shows results obtained when only water containing no toxin is applied (in a comparative test).

EXAMPLE 5

Insecticidal Effects on Other Coleopterans

The insecticidal activity of Buibui strain was examined, using larvae in the first instar of *Anomala albopilosa,* larvae in the first instar of *Anomala daimiana,* larvae in the first instar of *Minela splendens,* larvae in the first instar of *Popillia japonica,* and larvae in the second instar of *Blitopertha orientalis*. The samples were young larvae hatched from eggs of adults collected outdoors and temporarily bred in a commercially available leaf mold.

The testing method was as follows: 1 gram of leaf mold dried and sterilized in a dry oven at 160° C. for 60 minutes was weighed with a cup having a lid and a capacity of about 30 ml. Buibui culture in a predetermined concentration was mixed into the cup and sufficiently stirred, and then one larva was placed therein. A plurality of such mixtures were prepared, and bred in a thermostatic chamber at 25° C. The death rate was checked on the 7th, 14th, and 21st days to determine potency of Buibui. The results are shown in Table 7.

TABLE 7

| Larvae | Toxin dosage 130 kDa protein μg/g leaf mold | Death rates (%) 7th | 14th | 21st day |
|---|---|---|---|---|
| *Anomala albopilosa* in first instar | 50 | 100 | 100 | 100 |
| | 0.1 | 0 | 0 | 0 |
| *Anomala daimiana* in first instar | 50 | 0 | 50 | 70 |
| | 0.1 | 25 | 25 | 25 |
| *Minela splendens* in first instar | 50 | 100 | 100 | 100 |
| | 0.1 | 0 | 100 | 100 |
| *Popillia japonica* in first instar | 50 | 100 | 100 | 100 |
| *Blitopertha orientalis* in second instar | 50 | 100 | 100 | 100 |

The number of samples were 8 and 5 for *Anomala daimiana* and *Blitopertha orientalis,* respectively, and 10 for all the others.

As noted above, Buibui strain showed insecticidal activity with respect to *Anomala albopilosa, Anomala daimiana, Minela splendens, Popillia japonica,* and *Blitopertha orientalis.* In the case of *Anomala daimiana,* the death rate was 70% after 21 days, which is lower than the rates of the other insects. However, no increase in the weight was observed, and it was obvious that the larvae of *Anomala daimiana* were to die in due course. Thus, although some delays were observed, the cessation of food intake is considered equivalent to death. Particularly important is the insecticidal property to kill what are known as Japanese beetles, which are causing a serious problem in the United States.

Having determined the activity with respect to several coleopterans, the fact that the activity with respect to Popillia, Minela, and Blitopertha species as well as Anomala species suggests that the subject cells are not limited in application to those insects listed in Tables 6 and 7 but are applicable to a wide variety of coleopteran pests.

EXAMPLE 6

Activity of Beta-Exotoxin

Some of Bacillus strain cells excrete into culture media beta-exotoxin, which is a nucleotide derivative. It has an insecticidal effect similar to that of toxin proteins. Beta-exotoxin shows teratogenic action with respect to larvae of house flies, which provides a basis for evaluating the activity of beta-exotoxin. However, as shown in Table 8, when a supernatant of culture was prepared from a medium of Buibui strain by a usual method and applied to house flies, Buibui strain showed no teratogenesis with their pupation rate and eclosion rate remaining unaffected. When the above treating medium of Buibui strain was applied to *Anomala cuprea* Hope, its larvae remained alive after lapse of 14 days as shown in Table 9. The results of this test show that the insecticidal effect of Buibui strain on *Anomala cuprea* Hope does not depend on beta-exotoxin.

That is, beta-exotoxin does not exist to the extent of influencing the test results.

TABLE 8

Effect of beta-exotoxin in *Buibui* strain culture medium on house flies

| | | pupation rate (%) | eclosion rate (%) |
|---|---|---|---|
| *Buibui* culture | | 86.7 | 80 |
| Standard beta- | 2 ppm | 90 | 0 |
| exotoxin | 0.2 ppm | 100 | 0 |
| Distilled water | | 93.3 | 93.3 |

TABLE 9

Insecticidal effect of *Buibui* strain culture medium on *Anomala cuprea* Hope

| | Death rates (%) | |
|---|---|---|
| | 7th day | 14th day |
| *Buibui* culture* | 0 | 0 |
| Distilled water | 0 | 0 |

*The above *Buibui* medium refers to the medium remaining after strain cells are removed from the medium by centrifugal separation.

EXAMPLE 7

Insertion of Toxin Gene into Plants

One aspect of the subject invention is the transformation of plants with genes coding for a coleopteran-active toxin. The transformed plants are resistant to attack by coleopterans.

Genes coding for coleopteran-active toxins, as disclosed herein, can be inserted into plant cells using a variety of techniques which are well known in the art. For example, a large number of cloning vectors comprising a replication system in *E. coli* and a marker that permits selection of the transformed cells are available for preparation for the insertion of foreign genes into higher plants. The vectors comprise, for example, pBR322, pUC series, M13mp series, pACYC184, etc. Accordingly, the sequence coding for the *B.t.* toxin can be inserted into the vector at a suitable restriction site. The resulting plasmid is used for transformation into *E. coli.* The *E. coli* cells are cultivated in a suitable nutrient medium, then harvested and lysed. The plasmid is recovered. Sequence analysis, restriction analysis, electrophoresis, and other biochemical-molecular biological methods are generally carried out as methods of analysis. After each manipulation, the DNA sequence used can be cleaved and joined to the next DNA sequence. Each plasmid sequence can be cloned in the same or other plasmids. Depending on the method of inserting desired genes into the plant, other DNA sequences may be necessary. If, for example, the Ti or Ri plasmid is used for the transformation of the plant cell, then at least the right border, but often the right and the left border of the Ti or Ri plasmid T-DNA, has to be joined as the flanking region of the genes to be inserted.

The use of T-DNA for the transformation of plant cells has been intensively researched and sufficiently described in EP 120 516; Hoekema (1985) In: *The Binary Plant Vector System,* Offset-durkkerij Kanters B. V., Alblasserdam, Chapter 5; Fraley et al., *Crit. Rev. Plant Sci.* 4:1–46; and An et al. (1985) *EMBO J.* 4:277–287.

Once the inserted DNA has been integrated in the genome, it is relatively stable there and, as a rule, does not come out again. It normally contains a selection marker that confers on the transformed plant cells resistance to a biocide or an antibiotic, such as kanamycin, G 418, bleomycin, hygromycin, or chloramphenicol, inter alia. The individually employed marker should accordingly permit the selection of transformed cells rather than cells that do not contain the inserted DNA.

A large number of techniques are available for inserting DNA into a plant host cell. Those techniques include transformation with T-DNA using *Agrobacterium tumefaciens* or *Agrobacterium rhizogenes* as transformation agent, fusion, injection, or electroporation as well as other possible methods. If agrobacteria are used for the transformation, the DNA to be inserted has to be cloned into special plasmids, namely either into an intermediate vector or into a binary vector. The intermediate vectors can be integrated into the Ti or Ri plasmid by homologous recombination owing to sequences that are homologous to sequences in the T-DNA. The Ti or Ri plasmid also comprises the vir region necessary for the transfer of the T-DNA. Intermediate vectors cannot replicate themselves in agrobacteria. The intermediate vector can be transferred into *Agrobacterium tumefaciens* by means of a helper plasmid (conjugation). Binary vectors can replicate themselves both in *E. coli* and in agrobacteria. They comprise a selection marker gene and a linker or polylinker which are framed by the right and left T-DNA border regions. They can be transformed directly into agrobacteria (Holsters et al. [1978] *Mol. Gen. Genet.* 163:181–187). The agrobacterium used as host cell is to comprise a plasmid carrying a vir region. The vir region is necessary for the transfer of the T-DNA into the plant cell. Additional T-DNA may be contained. The bacterium so transformed is used for the transformation of plant cells. Plant explants can advantageously be cultivated with *Agrobacterium tumefaciens* or *Agrobacterium rhizogenes* for the transfer of the DNA into the plant cell. Whole plants can then be regenerated from the infected plant material (for example, pieces of leaf, segments of stalk, roots, but also protoplasts or suspension-cultivated cells) in a suitable medium, which may contain antibiotics or biocides for selection. The plants so obtained can then be tested for the presence of the inserted DNA. No special demands are made of the plasmids in the case of injection and electroporation. It is possible to use ordinary plasmids, such as, for example, pUC derivatives.

The transformed cells grow inside the plants in the usual manner. They can form germ cells and transmit the transformed trait(s) to progeny plants. Such plants can be grown in the normal manner and crossed with plants that have the same transformed hereditary factors or other hereditary factors. The resulting hybrid individuals have the corresponding phenotypic properties.

EXAMPLE 8

Cloning of Novel *B. thuringiensis* Genes into Insect Viruses

A number of viruses are known to infect insects. These viruses include, for example, baculoviruses and entomopoxviruses. In one embodiment of the subject invention, ant-active genes, as described herein, can be placed with the genome of the insect virus, thus enhancing the pathogenicity of the virus. Methods for constructing insect viruses which comprise *B.t.* toxin genes are well known and readily practiced by those skilled in the art. These procedures are described, for example, in Merryweather et al. (Merryweather, A. T., U. Weyer, M. P. G. Harris, M. Hirst, T. Booth, R. D. Possee (1990) *J. Gen. Virol.* 71:1535–1544) and Martens et al. (Martens, J. W. M., G. Honee, D. Zuidema, J. W. M. van Lent, B. Visser, J. M. Vlak (1990) *Appl. Environmental Microbiol.* 56(9):2764–2770).

It should be understood that the examples and embodiments described herein are for illustrative purposes only and that various modifications or changes in light thereof will be suggested to persons skilled in the art and are to be included within the spirit and purview of this application and the scope of the appended claims.

We claim:

1. A biologically pure culture of *Bacillus thuringiensis* having the identifying pesticidal characteristics of *Bacillus thuringiensis* serovar *japonensis* variety Buibui (FERM BP-3465).

2. A nucleotide sequence which codes for a toxin having activity against coleopterans wherein said nucleotide sequence codes for all or part of the amino acid sequence in SEQ ID NO. 2, comprises all or part of the sequence of SEQ ID NO. 1, or is sufficiently homologous to the sequence of SEQ ID NO. 1 to hybridize with the sequence of SEQ ID NO. 1.

3. The nucleotide sequence, according to claim 2, wherein said sequence codes for a coleopteran-active toxin which comprises all or part of the amino acid sequence of SEQ ID NO. 2.

4. A microorganism transformed with a nucleotide sequence of claim 2.

5. Treated, substantially intact cells containing an intracellular toxin, which toxin is a gene expression product of a nucleotide sequence of claim 2, wherein said cells are treated under conditions which prolong the insecticidal activity when said cells are applied to the environment of a target insect.

6. An insecticidal composition comprising as an active ingredient a toxin coded for by a nucleotide sequence of claim 2, and an agriculturally acceptable carrier.

7. A method for controlling coleopteran insects which comprises administering to said insects or to the environment of said insects a toxin expressed by a nucleotide sequence of claim 2.

8. The nucleotide sequence, according to claim 3, wherein said sequence comprises all or part of the nucleotide sequence of SEQ ID NO. 1.

9. The insecticidal composition, according to claim 6, wherein said composition comprises a microorganism of claim 4.

10. The insecticidal composition, according to claim 6, wherein said toxin is present in a *Bacillus thuringiensis* Buibui, and wherein said composition is diluted with water for spraying in liquid form.

11. The insecticidal composition, according to claim 10, wherein said *Bacillus thuringiensis* Buibui is cultured in media including NYS, L-broth, bouillon medium, solid media such as fish meal and soy bean powder, and wastes from starch or sugar processing such as corn syrup and corn steep.

12. The insecticidal composition, according to claim 10, which further comprises an antiseptic and an extender.

13. The insecticidal composition, according to claim 12, wherein said composition is reduced to powder form by a spray dryer.

14. The method, according to claim 7, wherein a microbe which expresses said toxin is administered to said insects or their environment.

15. A plant transformed with a nucleotide sequence which codes for a toxin having activity against coleopterans wherein said nucleotide sequence codes for all or part of the amino acid sequence in SEQ ID NO. 2, comprises all or part of the sequence of SEQ ID NO. 1, or is sufficiently homologous to the sequence of SEQ ID NO. 1 to hybridize with the sequence of SEQ ID NO. 1.

* * * * *

UNITED STATES PATENT AND TRADEMARK OFFICE
CERTIFICATE OF CORRECTION

PATENT NO. : 5,824,878

DATED : October 20, 1998

INVENTOR(S) : Ohba *et al.*

It is certified that error appears in the above-identifie d patent and that said Letters Patent is hereby corrected as shown below:

Column 3, line 34: "*Coli*" should read --*coli*--.

Column 5, line 13: "antigens.*japonensis*" should read --antigens. *Japonensis*--; and line 39: "*japonensis*" should read --*Japonensis*--.

Column 6, line 30: "*Bombyx mon*" should read --*Bombyx mori*--.

Column 10, line 17: "include Theological" should read --include rheological--.

Signed and Sealed this

Twentieth Day of April, 1999

Attest:

Q. TODD DICKINSON

*Attesting Officer* *Acting Commissioner of Patents and Trademarks*

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 3797 base pairs
( B ) TYPE: nucleic acid
( C ) STRANDEDNESS: single
( D ) TOPOLOGY: linear ( i i ) MOLECULE TYPE: DNA (genomic)

( v i ) ORIGINAL SOURCE:
( A ) ORGANISM: Bacillus thuringiensis
( B ) STRAIN: japonensis
( C ) INDIVIDUAL ISOLATE: Buibui ( i x ) FEATURE:
( A ) NAME/KEY: CDS
( B ) LOCATION: 187..3636

( x i ) SEQUENCE DESCRIPTION: SEQ ID NO:1:

```
AATTCTAATG ACACAGTAGA ATATTTTTAA AATAAAGATG GAAGGGGGAA TATGAAAAAA     60

ATATAATCAT AAGAGTCATA CAAAAAGATT GTATGTTAAA ACAAAAAAAT CCTGTAGGAA    120

TAGGGGTTTA AAAGCAATCA TTTGAAAAGA TAGTTATATT AAATTGTATG TATAGGGGGA    180

AAAAAG ATG AGT CCA AAT AAT CAA AAT GAG TAT GAA ATT ATA GAT GCT      228
       Met Ser Pro Asn Asn Gln Asn Glu Tyr Glu Ile Ile Asp Ala
        1               5                  10

TTA TCA CCC ACT TCT GTA TCC GAT AAT TCT ATT AGA TAT CCT TTA GCA     276
Leu Ser Pro Thr Ser Val Ser Asp Asn Ser Ile Arg Tyr Pro Leu Ala
 15                  20                  25                  30

AAC GAT CAA ACG AAC ACA TTA CAA AAC ATG AAT TAT AAA GAT TAT CTG     324
Asn Asp Gln Thr Asn Thr Leu Gln Asn Met Asn Tyr Lys Asp Tyr Leu
                 35                  40                  45

AAA ATG ACC GAA TCA ACA AAT GCT GAA TTG TCT CGA AAT CCC GGG ACA     372
Lys Met Thr Glu Ser Thr Asn Ala Glu Leu Ser Arg Asn Pro Gly Thr
             50                  55                  60

TTT ATT AGT GCG CAG GAT GCG GTT GGA ACT GGA ATT GAT ATT GTT AGT     420
Phe Ile Ser Ala Gln Asp Ala Val Gly Thr Gly Ile Asp Ile Val Ser
         65                  70                  75

ACT ATA ATA AGT GGT TTA GGG ATT CCA GTG CTT GGG GAA GTC TTC TCA     468
Thr Ile Ile Ser Gly Leu Gly Ile Pro Val Leu Gly Glu Val Phe Ser
     80                  85                  90

ATT CTG GGT TCA TTA ATT GGC TTA TTG TGG CCG TCA AAT AAT GAA AAT     516
Ile Leu Gly Ser Leu Ile Gly Leu Leu Trp Pro Ser Asn Asn Glu Asn
 95                 100                 105                 110

GTA TGG CAA ATA TTT ATG AAT CGA GTG GAA GAG CTA ATT GAT CAA AAA     564
Val Trp Gln Ile Phe Met Asn Arg Val Glu Glu Leu Ile Asp Gln Lys
                115                 120                 125

ATA TTA GAT TCT GTA AGA TCA AGA GCC ATT GCA GAT TTA GCT AAT TCT     612
Ile Leu Asp Ser Val Arg Ser Arg Ala Ile Ala Asp Leu Ala Asn Ser
            130                 135                 140
```

-continued

AGA ATA GCT GTA GAG TAC TAT CAA AAT GCA CTT GAA GAC TGG AGA AAA 660
Arg Ile Ala Val Glu Tyr Tyr Gln Asn Ala Leu Glu Asp Trp Arg Lys
145 150 155

AAC CCA CAC AGT ACA CGA AGC GCA GCA CTT GTA AAG GAA AGA TTT GGA 708
Asn Pro His Ser Thr Arg Ser Ala Ala Leu Val Lys Glu Arg Phe Gly
160 165 170

AAT GCA GAA GCA ATT TTA CGT ACT AAC ATG GGT TCA TTT TCT CAA ACG 756
Asn Ala Glu Ala Ile Leu Arg Thr Asn Met Gly Ser Phe Ser Gln Thr
175 180 185 190

AAT TAT GAG ACT CCA CTC TTA CCC ACA TAT GCA CAG GCC GCC TCT CTG 804
Asn Tyr Glu Thr Pro Leu Leu Pro Thr Tyr Ala Gln Ala Ala Ser Leu
195 200 205

CAT TTG CTT GTA ATG AGG GAT GTT CAA ATT TAC GGG AAG GAA TGG GGA 852
His Leu Leu Val Met Arg Asp Val Gln Ile Tyr Gly Lys Glu Trp Gly
210 215 220

TAT CCT CAA AAT GAT ATT GAC CTA TTT TAT AAA GAA CAA GTA TCT TAT 900
Tyr Pro Gln Asn Asp Ile Asp Leu Phe Tyr Lys Glu Gln Val Ser Tyr
225 230 235

ACG GCT AGA TAT TCC GAT CAT TGC GTC CAA TGG TAC AAT GCT GGT TTA 948
Thr Ala Arg Tyr Ser Asp His Cys Val Gln Trp Tyr Asn Ala Gly Leu
240 245 250

AAT AAA TTA AGA GGA ACG GGT GCT AAG CAA TGG GTG GAT TAT AAT CGT 996
Asn Lys Leu Arg Gly Thr Gly Ala Lys Gln Trp Val Asp Tyr Asn Arg
255 260 265 270

TTC CGA AGA GAA ATG AAT GTG ATG GTA TTG GAT CTA GTT GCA TTA TTT 1044
Phe Arg Arg Glu Met Asn Val Met Val Leu Asp Leu Val Ala Leu Phe
275 280 285

CCA AAC TAC GAT GCG CGT ATA TAT CCA CTG GAA ACA AAT GCA GAA CTT 1092
Pro Asn Tyr Asp Ala Arg Ile Tyr Pro Leu Glu Thr Asn Ala Glu Leu
290 295 300

ACA AGA GAA ATT TTC ACA GAT CCT GTT GGA AGT TAC GTA ACT GGA CAA 1140
Thr Arg Glu Ile Phe Thr Asp Pro Val Gly Ser Tyr Val Thr Gly Gln
305 310 315

TCG AGT ACC CTT ATA TCT TGG TAC GAT ATG ATT CCA GCA GCT CTT CCT 1188
Ser Ser Thr Leu Ile Ser Trp Tyr Asp Met Ile Pro Ala Ala Leu Pro
320 325 330

TCA TTT TCA ACG CTC GAG AAC CTA CTT AGA AAA CCT GAT TTC TTT ACT 1236
Ser Phe Ser Thr Leu Glu Asn Leu Leu Arg Lys Pro Asp Phe Phe Thr
335 340 345 350

TTG CTG CAA GAA ATT AGA ATG TAT ACA AGT TTT AGA CAA AAC GGT ACG 1284
Leu Leu Gln Glu Ile Arg Met Tyr Thr Ser Phe Arg Gln Asn Gly Thr
355 360 365

ATT GAA TAT TAT AAT TAT TGG GGA GGA CAA AGG TTA ACC CTT TCT TAT 1332
Ile Glu Tyr Tyr Asn Tyr Trp Gly Gly Gln Arg Leu Thr Leu Ser Tyr
370 375 380

ATC TAT GGT TCC TCA TTC AAT AAA TAT AGT GGG GTT CTT GCC GGT GCT 1380
Ile Tyr Gly Ser Ser Phe Asn Lys Tyr Ser Gly Val Leu Ala Gly Ala
385 390 395

GAG GAT ATT ATT CCT GTG GGT CAA AAT GAT ATT TAC AGA GTT GTA TGG 1428
Glu Asp Ile Ile Pro Val Gly Gln Asn Asp Ile Tyr Arg Val Val Trp
400 405 410

ACT TAT ATA GGA AGG TAC ACG AAT AGT CTG CTA GGA GTA AAT CCA GTT 1476
Thr Tyr Ile Gly Arg Tyr Thr Asn Ser Leu Leu Gly Val Asn Pro Val
415 420 425 430

ACT TTT TAC TTC AGT AAT AAT ACA CAA AAA ACT TAT TCG AAG CCA AAA 1524
Thr Phe Tyr Phe Ser Asn Asn Thr Gln Lys Thr Tyr Ser Lys Pro Lys
435 440 445

CAA TTC GCG GGT GGA ATA AAA ACA ATT GAT TCC GGC GAA GAA TTA ACT 1572
Gln Phe Ala Gly Gly Ile Lys Thr Ile Asp Ser Gly Glu Glu Leu Thr
450 455 460

-continued

```
TAC GAA AAT TAT CAA TCT TAT AGT CAC AGG GTA AGT TAC ATT ACA TCT     1620
Tyr Glu Asn Tyr Gln Ser Tyr Ser His Arg Val Ser Tyr Ile Thr Ser
        465                 470                 475

TTT GAA ATA AAA AGT ACC GGT GGT ACA GTA TTA GGA GTA GTT CCT ATA     1668
Phe Glu Ile Lys Ser Thr Gly Gly Thr Val Leu Gly Val Val Pro Ile
    480                 485                 490

TTT GGT TGG ACG CAT AGT AGT GCC AGT CGC AAT AAC TTT ATT TAC GCA     1716
Phe Gly Trp Thr His Ser Ser Ala Ser Arg Asn Asn Phe Ile Tyr Ala
495                 500                 505                 510

ACA AAA ATC TCA CAA ATC CCA ATC AAT AAA GCA AGT AGA ACT AGC GGT     1764
Thr Lys Ile Ser Gln Ile Pro Ile Asn Lys Ala Ser Arg Thr Ser Gly
                515                 520                 525

GGA GCG GTT TGG AAT TTC CAA GAA GGT CTA TAT AAT GGA GGA CCT GTA     1812
Gly Ala Val Trp Asn Phe Gln Glu Gly Leu Tyr Asn Gly Gly Pro Val
            530                 535                 540

ATG AAA TTA TCT GGG TCT GGT TCC CAA GTA ATA AAC TTA AGG GTC GCA     1860
Met Lys Leu Ser Gly Ser Gly Ser Gln Val Ile Asn Leu Arg Val Ala
        545                 550                 555

ACA GAT GCA AAG GGA GCA AGT CAA AGA TAT CGT ATT AGA ATC AGA TAT     1908
Thr Asp Ala Lys Gly Ala Ser Gln Arg Tyr Arg Ile Arg Ile Arg Tyr
    560                 565                 570

GCC TCT GAT AGA GCG GGT AAA TTT ACG ATA TCT TCC AGA TCT CCA GAG     1956
Ala Ser Asp Arg Ala Gly Lys Phe Thr Ile Ser Ser Arg Ser Pro Glu
575                 580                 585                 590

AAT CCT GCA ACC TAT TCA GCT TCT ATT GCT TAT ACA AAT ACT ATG TCT     2004
Asn Pro Ala Thr Tyr Ser Ala Ser Ile Ala Tyr Thr Asn Thr Met Ser
                595                 600                 605

ACA AAT GCT TCT CTA ACG TAT AGT ACT TTT GCA TAT GCA GAA TCT GGC     2052
Thr Asn Ala Ser Leu Thr Tyr Ser Thr Phe Ala Tyr Ala Glu Ser Gly
            610                 615                 620

CCT ATA AAC TTA GGG ATT TCG GGA AGT TCA AGG ACT TTT GAT ATA TCT     2100
Pro Ile Asn Leu Gly Ile Ser Gly Ser Ser Arg Thr Phe Asp Ile Ser
        625                 630                 635

ATT ACA AAA GAA GCA GGT GCT GCT AAC CTT TAT ATT GAT AGA ATT GAA     2148
Ile Thr Lys Glu Ala Gly Ala Ala Asn Leu Tyr Ile Asp Arg Ile Glu
    640                 645                 650

TTT ATT CCA GTT AAT ACG TTA TTT GAA GCA GAA GAA GAC CTA GAT GTG     2196
Phe Ile Pro Val Asn Thr Leu Phe Glu Ala Glu Glu Asp Leu Asp Val
655                 660                 665                 670

GCA AAG AAA GCT GTG AAT GGC TTG TTT ACG AAT GAA AAA GAT GCC TTA     2244
Ala Lys Lys Ala Val Asn Gly Leu Phe Thr Asn Glu Lys Asp Ala Leu
                675                 680                 685

CAG ACA AGT GTA ACG GAT TAT CAA GTC AAT CAA GCG GCA AAC TTA ATA     2292
Gln Thr Ser Val Thr Asp Tyr Gln Val Asn Gln Ala Ala Asn Leu Ile
            690                 695                 700

GAA TGC CTA TCC GAT GAG TTA TAC CCA AAT GAA AAA CGA ATG TTA TGG     2340
Glu Cys Leu Ser Asp Glu Leu Tyr Pro Asn Glu Lys Arg Met Leu Trp
        705                 710                 715

GAT GCA GTG AAA GAG GCG AAA CGA CTT GTT CAG GCA CGT AAC TTA CTC     2388
Asp Ala Val Lys Glu Ala Lys Arg Leu Val Gln Ala Arg Asn Leu Leu
    720                 725                 730

CAA GAT ACA GGC TTT AAT AGG ATT AAT GGA GAA AAC GGA TGG ACG GGA     2436
Gln Asp Thr Gly Phe Asn Arg Ile Asn Gly Glu Asn Gly Trp Thr Gly
735                 740                 745                 750

AGT ACG GGA ATC GAG GTT GTG GAA GGA GAT GTT CTG TTT AAA GAT CGT     2484
Ser Thr Gly Ile Glu Val Val Glu Gly Asp Val Leu Phe Lys Asp Arg
                755                 760                 765

TCG CTT CGT TTG ACA AGT GCG AGA GAG ATT GAT ACA GAA ACA TAT CCA     2532
Ser Leu Arg Leu Thr Ser Ala Arg Glu Ile Asp Thr Glu Thr Tyr Pro
            770                 775                 780
```

-continued

```
ACG TAT CTC TAT CAA CAA ATA GAT GAA TCG CTT TTA AAA CCA TAT ACA     2580
Thr Tyr Leu Tyr Gln Gln Ile Asp Glu Ser Leu Leu Lys Pro Tyr Thr
        785                 790                 795

AGA TAT AAA CTA AAA GGT TTT ATA GGA AGT AGT CAA GAT TTA GAG ATT     2628
Arg Tyr Lys Leu Lys Gly Phe Ile Gly Ser Ser Gln Asp Leu Glu Ile
    800                 805                 810

AAA TTA ATA CGT CAT CGG GCA AAT CAA ATC GTC AAA AAT GTA CCA GAT     2676
Lys Leu Ile Arg His Arg Ala Asn Gln Ile Val Lys Asn Val Pro Asp
815                 820                 825                 830

AAT CTC TTG CCA GAT GTA CGC CCT GTC AAT TCT TGT GGT GGA GTC GAT     2724
Asn Leu Leu Pro Asp Val Arg Pro Val Asn Ser Cys Gly Gly Val Asp
                835                 840                 845

CGC TGC AGT GAA CAA CAG TAT GTA GAC GCG AAT TTA GCA CTC GAA AAC     2772
Arg Cys Ser Glu Gln Gln Tyr Val Asp Ala Asn Leu Ala Leu Glu Asn
            850                 855                 860

AAT GGA GAA AAT GGA AAT ATG TCT TCT GAT TCC CAT GCA TTT TCT TTC     2820
Asn Gly Glu Asn Gly Asn Met Ser Ser Asp Ser His Ala Phe Ser Phe
        865                 870                 875

CAT ATT GAT ACG GGT GAA ATA GAT TTG AAT GAA AAT ACA GGA ATT TGG     2868
His Ile Asp Thr Gly Glu Ile Asp Leu Asn Glu Asn Thr Gly Ile Trp
    880                 885                 890

ATC GTA TTT AAA ATT CCG ACA ACA AAT GGA AAC GCA ACA CTA GGA AAT     2916
Ile Val Phe Lys Ile Pro Thr Thr Asn Gly Asn Ala Thr Leu Gly Asn
895                 900                 905                 910

CTT GAA TTT GTA GAA GAG GGG CCA TTG TCA GGG GAA ACA TTA GAA TGG     2964
Leu Glu Phe Val Glu Glu Gly Pro Leu Ser Gly Glu Thr Leu Glu Trp
                915                 920                 925

GCC CAA CAA CAA GAA CAA CAA TGG CAA GAC AAA ATG GCA AGA AAA CGT     3012
Ala Gln Gln Gln Glu Gln Gln Trp Gln Asp Lys Met Ala Arg Lys Arg
            930                 935                 940

GCA GCA TCA GAA AAA ACA TAT TAT GCA GCA AAG CAA GCC ATT GAT CGT     3060
Ala Ala Ser Glu Lys Thr Tyr Tyr Ala Ala Lys Gln Ala Ile Asp Arg
        945                 950                 955

TTA TTC GCA GAT TAT CAA GAC CAA AAA CTT AAT TCT GGT GTA GAA ATG     3108
Leu Phe Ala Asp Tyr Gln Asp Gln Lys Leu Asn Ser Gly Val Glu Met
    960                 965                 970

TCA GAT TTG TTG GCA GCC CAA AAC CTT GTA CAG TCC ATT CCT TAC GTA     3156
Ser Asp Leu Leu Ala Ala Gln Asn Leu Val Gln Ser Ile Pro Tyr Val
975                 980                 985                 990

TAT AAT GAT GCG TTA CCG GAA ATC CCT GGA ATG AAC TAT ACG AGT TTT     3204
Tyr Asn Asp Ala Leu Pro Glu Ile Pro Gly Met Asn Tyr Thr Ser Phe
                995                 1000                1005

ACA GAG TTA ACA AAT AGA CTC CAA CAA GCA TGG AAT TTG TAT GAT CTT     3252
Thr Glu Leu Thr Asn Arg Leu Gln Gln Ala Trp Asn Leu Tyr Asp Leu
            1010                1015                1020

CAA AAC GCT ATA CCA AAT GGA GAT TTT CGA AAT GGA TTA AGT AAT TGG     3300
Gln Asn Ala Ile Pro Asn Gly Asp Phe Arg Asn Gly Leu Ser Asn Trp
        1025                1030                1035

AAT GCA ACA TCA GAT GTA AAT GTG CAA CAA CTA AGC GAT ACA TCT GTC     3348
Asn Ala Thr Ser Asp Val Asn Val Gln Gln Leu Ser Asp Thr Ser Val
    1040                1045                1050

CTT GTC ATT CCA AAC TGG AAT TCT CAA GTG TCA CAA CAA TTT ACA GTT     3396
Leu Val Ile Pro Asn Trp Asn Ser Gln Val Ser Gln Gln Phe Thr Val
1055                1060                1065                1070

CAA CCG AAT TAT AGA TAT GTG TTA CGT GTC ACA GCG AGA AAA GAG GGA     3444
Gln Pro Asn Tyr Arg Tyr Val Leu Arg Val Thr Ala Arg Lys Glu Gly
                1075                1080                1085

GTA GGA GAC GGA TAT GTG ATC ATC CGT GAT GGT GCA AAT CAG ACA GAA     3492
Val Gly Asp Gly Tyr Val Ile Ile Arg Asp Gly Ala Asn Gln Thr Glu
            1090                1095                1100
```

```
ACA CTC ACA TTT AAT ATA TGT GAT GAT GAT ACA GGT GTT TTA TCT ACT      3540
Thr Leu Thr Phe Asn Ile Cys Asp Asp Asp Thr Gly Val Leu Ser Thr
        1105                1110                1115

GAT CAA ACT AGC TAT ATC ACA AAA ACA GTG GAA TTC ACT CCA TCT ACA      3588
Asp Gln Thr Ser Tyr Ile Thr Lys Thr Val Glu Phe Thr Pro Ser Thr
    1120                1125                1130

GAG CAA GTT TGG ATT GAC ATG AGT GAG ACC GAA GTG
Glu Gln Val Trp Ile Asp Met Ser Glu Thr Glu Val
1135                1140                1145

                                            TAT TCA ACA TAGAAATGT    3643
                                            Tyr Ser Thr
                                                    1149

AGAACTCGTG TTAGAAGAAG AGTAATCATA GTTTCCCTCC AGATAGAAGG TTGATCTGGA    3703

GGTTTTCTTA TAGAGAGAGT ACTATGAATC AAATGTTTGA TGAATGCGTT GCGAGCGGTT    3763

TATCTCAAAT ATCAACGGTA CAAGGTTTAT AAAT                                3797
```

( 2 ) INFORMATION FOR SEQ ID NO:2:

( i ) SEQUENCE CHARACTERISTICS:
( A ) LENGTH: 1149 amino acids
( B ) TYPE: amino acid
( D ) TOPOLOGY: linear ( i i ) MOLECULE TYPE: protein ( x i ) SEQUENCE DESCRIPTION: SEQ ID NO:2:

```
Met Ser Pro Asn Asn Gln Asn Glu Tyr Glu Ile Ile Asp Ala Leu Ser
  1               5                  10                  15

Pro Thr Ser Val Ser Asp Asn Ser Ile Arg Tyr Pro Leu Ala Asn Asp
             20                  25                  30

Gln Thr Asn Thr Leu Gln Asn Met Asn Tyr Lys Asp Tyr Leu Lys Met
         35                  40                  45

Thr Glu Ser Thr Asn Ala Glu Leu Ser Arg Asn Pro Gly Thr Phe Ile
     50                  55                  60

Ser Ala Gln Asp Ala Val Gly Thr Gly Ile Asp Ile Val Ser Thr Ile
 65                  70                  75                  80

Ile Ser Gly Leu Gly Ile Pro Val Leu Gly Glu Val Phe Ser Ile Leu
                 85                  90                  95

Gly Ser Leu Ile Gly Leu Leu Trp Pro Ser Asn Asn Glu Asn Val Trp
            100                 105                 110

Gln Ile Phe Met Asn Arg Val Glu Glu Leu Ile Asp Gln Lys Ile Leu
        115                 120                 125

Asp Ser Val Arg Ser Arg Ala Ile Ala Asp Leu Ala Asn Ser Arg Ile
    130                 135                 140

Ala Val Glu Tyr Tyr Gln Asn Ala Leu Glu Asp Trp Arg Lys Asn Pro
145                 150                 155                 160

His Ser Thr Arg Ser Ala Ala Leu Val Lys Glu Arg Phe Gly Asn Ala
                165                 170                 175

Glu Ala Ile Leu Arg Thr Asn Met Gly Ser Phe Ser Gln Thr Asn Tyr
            180                 185                 190

Glu Thr Pro Leu Leu Pro Thr Tyr Ala Gln Ala Ala Ser Leu His Leu
        195                 200                 205

Leu Val Met Arg Asp Val Gln Ile Tyr Gly Lys Glu Trp Gly Tyr Pro
    210                 215                 220

Gln Asn Asp Ile Asp Leu Phe Tyr Lys Glu Gln Val Ser Tyr Thr Ala
225                 230                 235                 240
```

-continued

Arg Tyr Ser Asp His Cys Val Gln Trp Tyr Asn Ala Gly Leu Asn Lys
245 250 255

Leu Arg Gly Thr Gly Ala Lys Gln Trp Val Asp Tyr Asn Arg Phe Arg
260 265 270

Arg Glu Met Asn Val Met Val Leu Asp Leu Val Ala Leu Phe Pro Asn
275 280 285

Tyr Asp Ala Arg Ile Tyr Pro Leu Glu Thr Asn Ala Glu Leu Thr Arg
290 295 300

Glu Ile Phe Thr Asp Pro Val Gly Ser Tyr Val Thr Gly Gln Ser Ser
305 310 315 320

Thr Leu Ile Ser Trp Tyr Asp Met Ile Pro Ala Ala Leu Pro Ser Phe
325 330 335

Ser Thr Leu Glu Asn Leu Leu Arg Lys Pro Asp Phe Phe Thr Leu Leu
340 345 350

Gln Glu Ile Arg Met Tyr Thr Ser Phe Arg Gln Asn Gly Thr Ile Glu
355 360 365

Tyr Tyr Asn Tyr Trp Gly Gly Gln Arg Leu Thr Leu Ser Tyr Ile Tyr
370 375 380

Gly Ser Ser Phe Asn Lys Tyr Ser Gly Val Leu Ala Gly Ala Glu Asp
385 390 395 400

Ile Ile Pro Val Gly Gln Asn Asp Ile Tyr Arg Val Val Trp Thr Tyr
405 410 415

Ile Gly Arg Tyr Thr Asn Ser Leu Leu Gly Val Asn Pro Val Thr Phe
420 425 430

Tyr Phe Ser Asn Asn Thr Gln Lys Thr Tyr Ser Lys Pro Lys Gln Phe
435 440 445

Ala Gly Gly Ile Lys Thr Ile Asp Ser Gly Glu Glu Leu Thr Tyr Glu
450 455 460

Asn Tyr Gln Ser Tyr Ser His Arg Val Ser Tyr Ile Thr Ser Phe Glu
465 470 475 480

Ile Lys Ser Thr Gly Gly Thr Val Leu Gly Val Val Pro Ile Phe Gly
485 490 495

Trp Thr His Ser Ser Ala Ser Arg Asn Asn Phe Ile Tyr Ala Thr Lys
500 505 510

Ile Ser Gln Ile Pro Ile Asn Lys Ala Ser Arg Thr Ser Gly Gly Ala
515 520 525

Val Trp Asn Phe Gln Glu Gly Leu Tyr Asn Gly Gly Pro Val Met Lys
530 535 540

Leu Ser Gly Ser Gly Ser Gln Val Ile Asn Leu Arg Val Ala Thr Asp
545 550 555 560

Ala Lys Gly Ala Ser Gln Arg Tyr Arg Ile Arg Ile Arg Tyr Ala Ser
565 570 575

Asp Arg Ala Gly Lys Phe Thr Ile Ser Ser Arg Ser Pro Glu Asn Pro
580 585 590

Ala Thr Tyr Ser Ala Ser Ile Ala Tyr Thr Asn Thr Met Ser Thr Asn
595 600 605

Ala Ser Leu Thr Tyr Ser Thr Phe Ala Tyr Ala Glu Ser Gly Pro Ile
610 615 620

Asn Leu Gly Ile Ser Gly Ser Ser Arg Thr Phe Asp Ile Ser Ile Thr
625 630 635 640

Lys Glu Ala Gly Ala Ala Asn Leu Tyr Ile Asp Arg Ile Glu Phe Ile
645 650 655

Pro Val Asn Thr Leu Phe Glu Ala Glu Glu Asp Leu Asp Val Ala Lys
660 665 670

-continued

Lys Ala Val Asn Gly Leu Phe Thr Asn Glu Lys Asp Ala Leu Gln Thr
675 680 685

Ser Val Thr Asp Tyr Gln Val Asn Gln Ala Ala Asn Leu Ile Glu Cys
690 695 700

Leu Ser Asp Glu Leu Tyr Pro Asn Glu Lys Arg Met Leu Trp Asp Ala
705 710 715 720

Val Lys Glu Ala Lys Arg Leu Val Gln Ala Arg Asn Leu Leu Gln Asp
725 730 735

Thr Gly Phe Asn Arg Ile Asn Gly Glu Asn Gly Trp Thr Gly Ser Thr
740 745 750

Gly Ile Glu Val Val Glu Gly Asp Val Leu Phe Lys Asp Arg Ser Leu
755 760 765

Arg Leu Thr Ser Ala Arg Glu Ile Asp Thr Glu Thr Tyr Pro Thr Tyr
770 775 780

Leu Tyr Gln Gln Ile Asp Glu Ser Leu Leu Lys Pro Tyr Thr Arg Tyr
785 790 795 800

Lys Leu Lys Gly Phe Ile Gly Ser Ser Gln Asp Leu Glu Ile Lys Leu
805 810 815

Ile Arg His Arg Ala Asn Gln Ile Val Lys Asn Val Pro Asp Asn Leu
820 825 830

Leu Pro Asp Val Arg Pro Val Asn Ser Cys Gly Gly Val Asp Arg Cys
835 840 845

Ser Glu Gln Gln Tyr Val Asp Ala Asn Leu Ala Leu Glu Asn Asn Gly
850 855 860

Glu Asn Gly Asn Met Ser Ser Asp Ser His Ala Phe Ser Phe His Ile
865 870 875 880

Asp Thr Gly Glu Ile Asp Leu Asn Glu Asn Thr Gly Ile Trp Ile Val
885 890 895

Phe Lys Ile Pro Thr Thr Asn Gly Asn Ala Thr Leu Gly Asn Leu Glu
900 905 910

Phe Val Glu Glu Gly Pro Leu Ser Gly Glu Thr Leu Glu Trp Ala Gln
915 920 925

Gln Gln Glu Gln Gln Trp Gln Asp Lys Met Ala Arg Lys Arg Ala Ala
930 935 940

Ser Glu Lys Thr Tyr Tyr Ala Ala Lys Gln Ala Ile Asp Arg Leu Phe
945 950 955 960

Ala Asp Tyr Gln Asp Gln Lys Leu Asn Ser Gly Val Glu Met Ser Asp
965 970 975

Leu Leu Ala Ala Gln Asn Leu Val Gln Ser Ile Pro Tyr Val Tyr Asn
980 985 990

Asp Ala Leu Pro Glu Ile Pro Gly Met Asn Tyr Thr Ser Phe Thr Glu
995 1000 1005

Leu Thr Asn Arg Leu Gln Gln Ala Trp Asn Leu Tyr Asp Leu Gln Asn
1010 1015 1020

Ala Ile Pro Asn Gly Asp Phe Arg Asn Gly Leu Ser Asn Trp Asn Ala
1025 1030 1035 1040

Thr Ser Asp Val Asn Val Gln Gln Leu Ser Asp Thr Ser Val Leu Val
1045 1050 1055

Ile Pro Asn Trp Asn Ser Gln Val Ser Gln Gln Phe Thr Val Gln Pro
1060 1065 1070

Asn Tyr Arg Tyr Val Leu Arg Val Thr Ala Arg Lys Glu Gly Val Gly
1075 1080 1085

Asp Gly Tyr Val Ile Ile Arg Asp Gly Ala Asn Gln Thr Glu Thr Leu

-continued

```
      1090                    1095                    1100

Thr Phe Asn Ile Cys Asp Asp Asp Thr Gly Val Leu Ser Thr Asp Gln
1105                1110                1115                1120

Thr Ser Tyr Ile Thr Lys Thr Val Glu Phe Thr Pro Ser Thr Glu Gln
                1125                1130                1135

Val Trp Ile Asp Met Ser Glu Thr Glu Val Tyr Ser Thr
            1140                1145
```